United States Patent [19]
DeWoskin

[11] Patent Number: 5,263,857
[45] Date of Patent: Nov. 23, 1993

[54] BREAKAWAY DEVICE FOR ORTHODONTIC TRACTION APPLIANCES

[75] Inventor: Irvin S. DeWoskin, St. Louis, Mo.

[73] Assignee: Orthoband Company, Inc., Barnhart, Mo.

[21] Appl. No.: 900,852

[22] Filed: Jun. 18, 1992

[51] Int. Cl.⁵ .............................................. A61C 3/00
[52] U.S. Cl. .................................................... 433/5
[58] Field of Search ............................................ 433/5

[56] References Cited

U.S. PATENT DOCUMENTS

| | | | |
|---|---|---|---|
| 3,212,637 | 7/1970 | Dougherty et al. | 433/5 |
| 4,087,915 | 5/1978 | Andrews. | |
| 4,115,921 | 9/1978 | Armstrong. | |
| 4,155,161 | 5/1979 | Armstrong. | |
| 4,215,983 | 8/1980 | Frazier | 433/5 |
| 4,226,589 | 10/1980 | Klein | 433/5 |
| 4,238,188 | 12/1980 | Armstrong | 433/5 |
| 4,734,032 | 3/1988 | DeWoskin | 433/5 |
| 5,030,088 | 7/1991 | Rogow | 433/5 |

Primary Examiner—Cary E. O'Connor
Assistant Examiner—Cindy A. Cherichetti
Attorney, Agent, or Firm—Senniger, Powers, Leavitt & Roedel

[57] ABSTRACT

A breakaway device for orthodontic traction appliances comprising a case having a spring clasp therein for releasably clasping a coupling member, the coupling member separating from the clasp when subjected to pull exceeding a predetermined value, with an adjustment for the clasp to adjust its grip on the coupling member for adjusting the breakaway pull.

15 Claims, 3 Drawing Sheets

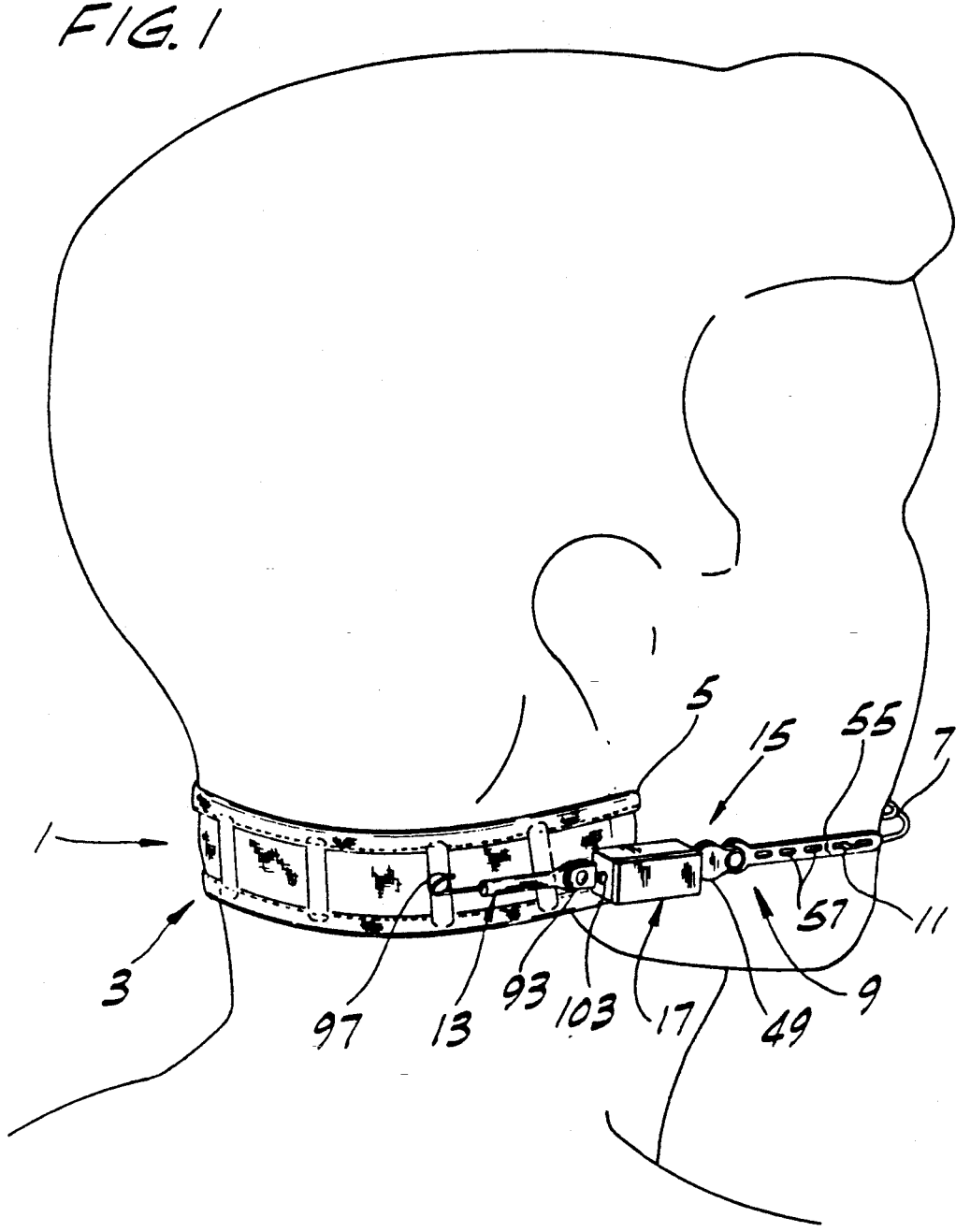

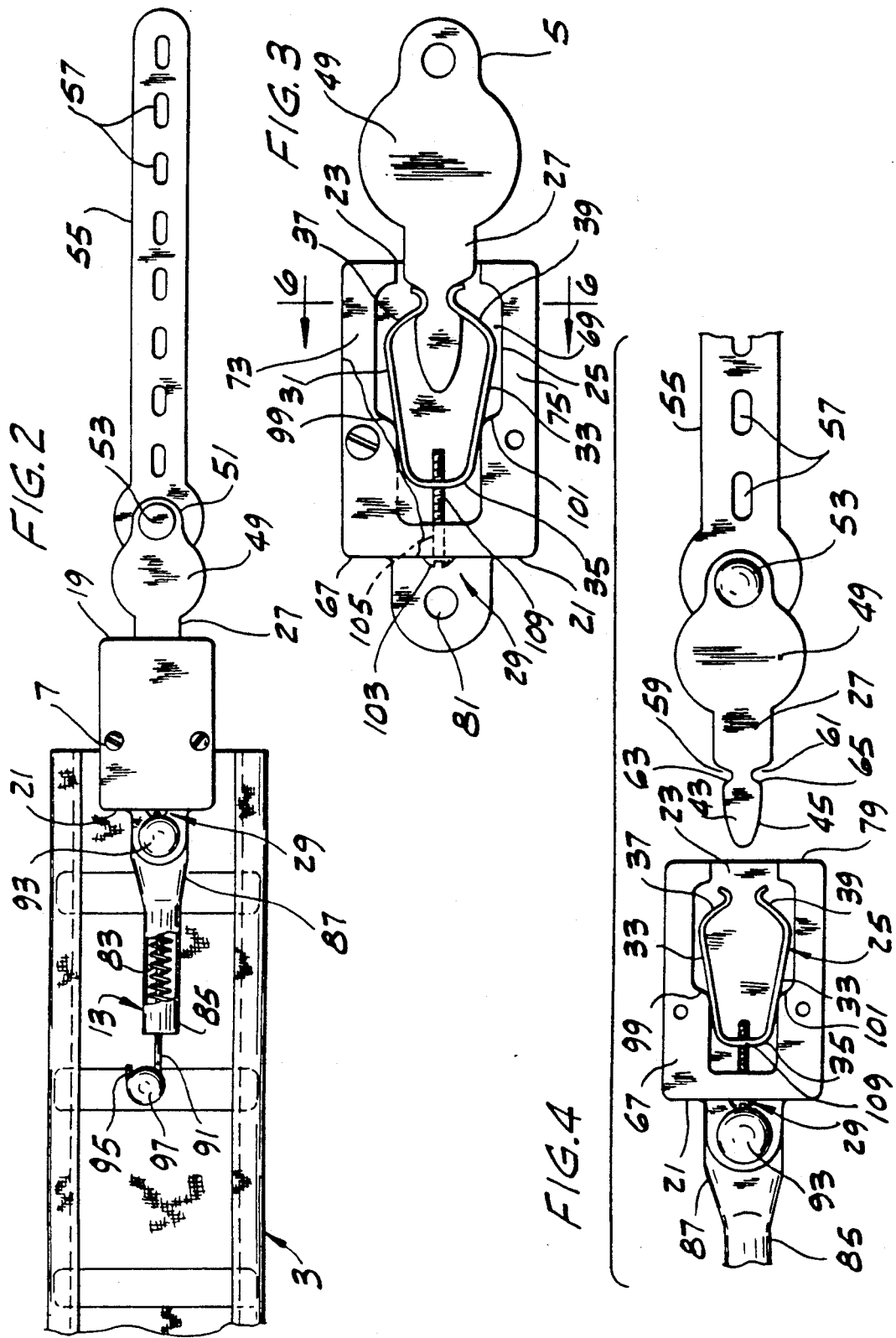

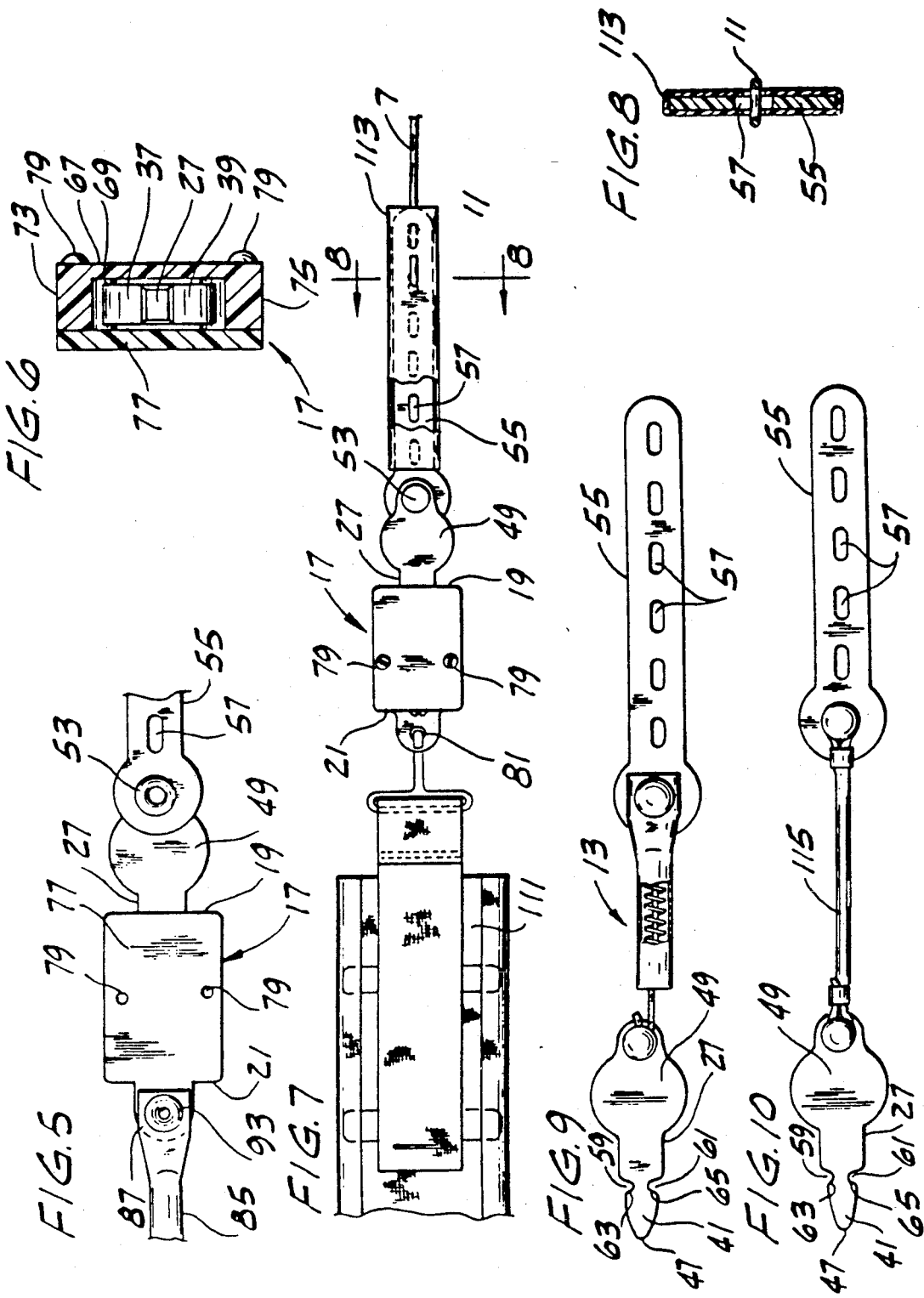

BREAKAWAY DEVICE FOR ORTHODONTIC TRACTION APPLIANCES

BRIEF SUMMARY OF THE INVENTION

This invention relates to a breakaway device for orthodontic traction appearances, being especially concerned with a breakaway device of the type disclosed in my coassigned U.S. Pat. No. 4,734,032 issued Mar. 9, 1958, entitled Orthodontic Traction Appliance, on which the present device is an improvement. Reference may also be made to U.S. Pat. Nos. 4,087,915 issued May 9, 1978, 4,115,921 issued Sep. 26, 1978, 4,155,161 issued May 22, 1979, 4,212,637 issued Jul. 15, 1980, 4,238,188, issued Dec. 9, 1980 and 4,226,589 issued Oct. 7, 1980 for other prior art on orthodontic traction appliances with a safety breakaway feature.

This invention, like the above-noted prior art, is especially concerned with orthodontic traction appliances of the type including headgear or a cervical strap and tension means secured to the headgear or cervical strap for exerting a pull via a face bow (an outer bow) on an arch wire (an inner bow) having free ends which are inserted in fixtures on certain of the patient's teeth to apply traction thereto. It addresses the problem discussed in U.S. Pat. Nos. 4,087,915 and 4,212,637 of avoiding injury to a patient wearing such an appliance, which may result in the event someone grasps, pulls and releases the face bow, resulting in the ends of the arch wire being pulled out of the fixtures and the arch wire springing back under the force of the tension means like a slingshot and the ends of the arch wire stabbing the patient.

Among the several objects of the invention may be noted the provision of a breakaway device of the class described which is adjustable for setting the breakaway force; the provision of such a device which is readily re-attachable after breakaway for subsequent wear of the appliance; and the provision of such a breakaway device which is relatively economical to manufacture and reliable in use.

In general, a breakaway device of this invention is incorporated in an orthodontic traction appliance, the appliance comprising support means e.g. a cervical pad or headgear to be worn by a patient, the support means having portions which are positioned adjacent the sides of the patient's head as the support means is worn by the patient, an orthodontic face bow, and means extending forward on opposite sides of the patient's head from said portions of the support means to a connection with the face bow for pulling back on the bow to apply traction to the teeth. The interconnecting means comprises tension means for applying the traction to the teeth and includes said breakaway device for separation of the interconnecting means when subjected to pull exceeding a predetermined value. The breakaway device comprises a relatively flat case which is positioned flatwise against the respective side of the patient's head as the appliance is worn by the patient, said case having anterior and posterior ends with an opening at one end thereof, and a coupling member for insertion in the case through said opening. Latch means in the case releasably latches the coupling member inserted in the case through said opening, said latch means comprising spring gripper means adapted resiliently to grip said coupling member and to release said coupling member for being pulled out of the case when subjected to breakaway pull exceeding a predetermined value, as determined by the spring grip of the gripper means on said member. Means is provided carried by the case accessible from outside the case for adjusting the grip of the spring gripper means on the coupling member to adjust the breakaway pull.

Other objects and features will be in part apparent and in part pointed out hereinafter.

BRIEF DESCRIPTION OF THE DRAWINGS

FIG. 1 is a perspective showing an orthodontic traction appliance, more particularly one including a cervical pad, as worn on the patient's head, which includes a breakaway device of this invention on each side of the patient's head;

FIG. 2 is a view in side elevation showing the breakaway device;

FIG. 3 is an enlarged view of a case and a coupling member of the breakaway device similar to FIG. 2 partly broken away to show the interior of the case, an showing the coupling member latched in the case;

FIG. 4 is an exploded view showing the case with a side wall removed and showing the coupling member pulled out of the case;

FIG. 5 is a view showing the other side of the case from FIG. 4 and showing the coupling member entered in the case;

FIG. 6 is a vertical section on line 6—6 of FIG. 3;

FIG. 7 is a view of a modification of the traction appliance with the breakaway device;

FIG. 8 is an enlarged section on line 8—8 of FIG. 7; and

FIGS. 9 and 10 are views of futher modifications.

Corresponding reference characters indicate corresponding parts throughout several views of the drawing.

DETAILED DESCRIPTION

Referring to the drawings, first more particularly to FIGS. 1-6, there is generally indicated at 1 an orthodontic traction appliance including support means 3 to be worn by a patient having end portions 5 which are positioned adjacent the sides of the patient's head, as the support means is worn. The support means may comprise a cervical pad or strap as disclosed in my aforesaid U.S. Pat. No. 4,734,032, which is incorporated herein by reference. The traction appliance, considered in its entirety, comprises the support means or cervical pad or strap 3, an orthodontic face bow 7, means denoted in its entirety by the reference numeral 9 extending forward on opposite sides of the patient's head from each said end portion 5 of the cervical strap 3 to connections such as indicated at 11 with the ends of the face bow for pulling back on the face bow to apply traction to the teeth for orthodontic purposes. Each said interconnecting means 9 includes tension means 13 for developing the tension for pulling back on the face bow for applying the traction to the teeth, and a breakaway device 15 of this invention for separation of the interconnecting means when subjected to pull exceeding a predetermined value (i.e. the breakaway pull).

The breakaway device comprises a relatively flat case 17 which is positioned flatwise against the respective side of the patient's head as the appliance 1 is worn by the patient. The case has anterior and posterior ends 19 and 21 with an opening 23 at one end, this end being the anterior end of the case, as illustrated in FIGS. 1-4. Latch means generally designated 25 is held in the case for releasably latching a coupling member or coupler 27 inserted in the anterior end 19 of the case through the opening 23. This latch means comprises spring gripper means adapted resiliently to grip the coupling member 27 and to release the coupling member for being pulled out of the case when subjected to breakaway pull exceeding a Predetermined value, as determined by the spring grip of the latch or spring gripper means 25 on the coupling member. At 29 is generally indicated means which is carried by the case and accessible from the outside of the case for adjusting the grip of the spring gripper means on the coupling member to adjust the breakaway pull.

More particularly, the latch or spring gripper means 25 comprises a generally V-shaped spring clasp having first and second arms 31 and 33 extending from an apex 35 forward in the case from adjacent the posterior (closed) end 21 of the case toward the anterior end 19 of the case (the end with the opening 23), the arms having free ends adjacent the end 19 of the case, with tips 37 and 39 which may be of the formation as shown in the drawings or the like extending inwardly toward one another at the free ends of the arms for releasably latching the coupling member 27 in the case. As the clasp 25 is positioned in the case, arm 31 is toward the top and arm 33 is toward the bottom of the case, and apex 35 of the clasp is adjacent the posterior end 21 of the case. The coupling member or coupler 27 comprises a relatively thin flat elongate member or tongue having an end portion or nose 41 generally of tapered form with inclined upper and lower edges 43 and 45 convergent to a narrow end 47. The relatively thin flat elongate member or tongue 27 extends from a flat head 49 which may be of circular shape, as shown, with a radially extending ear 51 opposite the tongue for interconnection at 53 with a flexible plastic strap 55 having a series of holes 57 therein for attachment to an end of a face bow. The tongue 27 has recesses 59 and 61 at top and bottom at the wide end of the tapered end portion or nose 41 providing shoulders 63 and 65 facing away from the nose, these shoulders being suitably angled for gripping the tongue while enabling release of the tongue on pull on the tongue exceeding a predetermined pull (i.e. the breakaway pull).

The case 17 comprises an elongate rectangular block 67 molded of plastic with a recess 69 in one side of the block defining a chamber for the clasp 25, and further defining one side wall 71 of the case 9 (which may constitute its inside wall which engages against the side of the patient's head as the appliance is worn), the anterior and posterior ends 19 and 21 of the case, and a top 73 and bottom 75 for the case. A second side wall 77 constituting a separate part from the block is secured as by screws 79 to the open side of the block closing off the recess or chamber 69. This second side wall has a posterior extension having a hole 81 for attachment to the posterior end of the case of the aforesaid tension means 13. As shown in FIG. 2, this tension means 13 is of the same type as shown in my U.S. Pat. Nos. 3,765,093, 3,772,789 and 4,121,341 comprising a compression spring 83 in a plastic tube 85, the tube being closed at one end as indicated at 87, and a rod 91 extending out of the other end of the tube and biased in the direction toward the closed end of the tube by the spring (forward as viewed in FIG. 2). As shown in FIG. 2, the tube is connected at its closed end to the extension of the side wall of the case by fastener 93 extending through the hole 81, and the rod 91 is formed at its outer end with a hook 95 by means of which it is hooked to a fastener 97 in the cervical pad 3.

The clasp 25 comprises a relatively narrow strip of resilient sheet metal bent generally to V-shape, thereby having the upper and lower arms 31 and 33 diverging from the apex 35, the latter being relatively flat rather than sharp. The arms are further bent to provide the tips 37 and 39 at the ends of the arms. The top and bottom of the case have a stepped formation providing cam means 99 and 101 at the top and bottom of the chamber 69 engaging the upper and lower arms of the clasp for contracting the arms (i.e., squeezing them together) on bodily movement of the clasp relative to the case toward the closed end 21 and allowing the arms to expand (under their inherent spring bias on movement of the clasp relative to the case toward its end with the opening 23. The aforesaid means 29 for adjusting the grip of the clasp on the coupling member 27 for adjusting the breakaway pull comprises a screw 103 extending through a hole 105 in the closed end 21 of the case, held in suitable manner against axial movement in the hole 105, and threaded as indicated at 109 in a tapped hole in the apex 35 of the clasp. The arrangement is such that on turning the screw in one direction, the clasp is moved in the direction toward the closed end of the case, resulting in squeezing together of the arms 31 and 33 of the clasp by their engagement with the cam means or steps 99 and 101 at the top and bottom of the case to increase the grip of the clasp on the coupling member 27, and on turning the screw in the opposite direction, the clasp is moved in the direction away from the closed end of the case, allowing the arms to expand to decrease the grip of the clasp on the coupling member.

In the use of the appliance 1 including the cervical pad 3, the pad with a traction assembly 9, comprising tension means 13, case 17, coupling means 27 and strap 55, attached to each end portion 5 of the pad, is placed around the back of the neck and the straps 55 of each of the two traction assemblies 9 are connected to the ends of the face bow as indicated at 11, the springs in the tension devices 13 being placed under compression to apply traction to the teeth via the face bow. A desired breakaway pull is set for the appliance by adjustment of the screws 103 of the breakaway devices in the two traction assemblies 9 to adjust the grip of the clasp 25 of each breakaway device on the respective coupling member 27. If the face bow should be pulled forward away from the patient's head with a pull or force exceeding the breakaway pull, the nose ends 41 of the coupling members 27 pull out of the clasps, thereby avoiding snap-back of the face bow for the patient's safety. The appliance is readily reassembled by entry of the nose ends 41 of the coupling members 27 in the cases of the two breakaway devices, the noses spreading the arms 31 and 33 of the clasps apart, and the arms springing back for entry of tips 37 and 39 of the arms into the recesses 59, 61 into the recesses releasably to grip the coupling members 27 in the cases.

FIG. 7 illustrates a modification wherein instead of using the spring type tension means 13, elastic straps such as indicated at 111 are interposed between the cervical pad 3 and the cases 17. Also, as shown in FIGS. 7 and 8, the strap may have a plastic sleeve 113 heat shrunk thereon overlying the series of holes 57 in the strap. The orthodontist may punch a hole in the sleeve at the hole in the strap selected for application of the desired traction on the teeth, thus enabling ready attachment of the strap to the ends of the face bow by the patient.

FIG. 9 illustrates an alternative arrangement wherein a spring device 13 is interposed between the strap 55 and the coupling member 27, instead of between the pad 3 and the case 17. In this arrangement, the breakaway case 17 is connected at its posterior end to the pad.

FIG. 10 illustrates another alternate arrangement similar to that of FIG. 9, but in which a tension means comprising a length of elastic cord 115 is used instead of a spring device 13.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A breakaway device for an orthodontic traction appliance, said appliance comprising support means to be worn by a patient, said support means having portions which are positioned adjacent the sides of the patient's head as the support means is worn by the patient, an orthodontic face bow, and means extending forward on opposite sides of the patient's head from said portions of the support means to a connection with the face bow for pulling back on the bow to apply traction to the teeth, said interconnecting means comprising tension means for applying the traction to the teeth and including said breakaway device for separation of the interconnecting means when subjected to pull exceeding a predetermined value, said breakaway device comprising:

a relatively flat case which is positioned flatwise against the respective side of the patient's head as the appliance is worn by the patient said case having anterior and posterior ends with an opening at one end thereof a coupling member for insertion in the case through said opening;

latch means in the case for releasably latching the coupling member inserted in the case through said opening;

said latch means comprising spring gripper means adapted resiliently to grip said coupling member and to release said coupling member for being pulled out of the case when subjected to breakaway pull exceeding a predetermined value, as determined by the spring grip of the gripper means on said member;

and means carried by the case accessible from outside the case for adjusting the grip of the spring gripper means on the coupling member to adjust the breakaway pull.

2. A breakaway device for an orthodontic traction appliance, said appliance comprising support means to be worn by a patient, said support means having portions which are positioned adjacent the sides of the patient's head as the support means is worn by the patient, an orthodontic face bow, and means extending forward on opposite sides of the patient's head from said portions of the support means to a connection with the face bow for pulling back on the bow to apply traction to the teeth, said interconnecting means comprising tension means for applying the traction to the teeth and including said breakaway device for separation of the interconnecting means when subjected to pull exceeding a predetermined value, said breakaway device comprising:

a relatively flat case which is positioned flatwise against the respective side of the patient's head as the appliance is worn by the patient:

said case having anterior and posterior ends with an opening at one end thereof;

a coupling member for insertion in the case through said opening;

latch means in the case for releasably latching the coupling member inserted in the case through said opening;

said latch means comprising spring gripper means adapted resiliently to grip said coupling member and to release said coupling member for being pulled out of the case when subjected to breakaway pull exceeding a predetermined value, as determined by the spring grip of the gripper means on said member;

and means carried by the case accessible from outside the case for adjusting the grip of the spring gripper means on the coupling member to adjust the breakaway pull;

wherein the spring gripper means comprises a spring clasp having first and second arms extending endwise in said case having free ends adjacent the said one end of the case with the opening, said arms being arranged to spring away one from the other on insertion of said coupling member between their free ends, the arms having means extending inwardly toward one another at their free ends for releasably latching the coupling member in the case and the coupling member having shoulders facing away from said one end of the case, the arms being resiliently contractible into a contracted position wherein said inwardly extending means are latched in place with respect to the shoulders to couple the case and the coupling member together for transmission of tension as long as the tension is less than said predetermined value, the coupling member spreading the arms apart and pulling out from between the arms when a pull on the interconnecting means exceeds the breakaway value.

3. A breakaway device as set forth in claim 2 wherein said adjusting means comprises means for adjusting the arms to vary the force required for the coupling member to spread the arms apart.

4. A breakaway device as set forth in claim 3 wherein the clasp comprises a relatively narrow strip of resilient sheet metal bent generally to V-shape, thereby having said arms diverging from an apex, and further bent to provide the said inwardly extending means at the ends of the arms, the case having a chamber therein for the clasp with the clasp being arranged in the chamber with its apex adjacent the other end of the case and with its arms extending in the case from adjacent said other end of the case to adjacent its said one end, the chamber having cam means at the top and bottom thereof engaging the top and bottom of the arms for contracting the arms on movement of the clasp relative to the case toward its said other end and allowing the arms to expand on movement of the clasp relative to the case toward its said one end, the adjusting means comprising an adjustment screw extending through said other end of the case to a connection with the apex of the clasp.

5. A breakaway device as set forth in claim 4 wherein the screw is threaded in a tapped hole in the apex of the clasp.

6. A breakaway device as set forth in claim 4 wherein the case comprises an elongate rectangular block molded of plastic with a recess in one side of said block, defining said chamber and further defining one side wall of the case constituting its inside as the appliance is worn, the posterior and anterior ends of the case and a top and bottom for the case, the case further comprising a second side wall constituting a separate part from the block secured to the block closing said chamber, said second side wall having an extension at the said other end of the case for attachment thereof in said appliance.

7. A breakaway device as set forth in claim 4 wherein said coupling member comprises a relatively thin flat elongate member having an end portion generally of tapered form with inclined upper and lower edges convergent to a narrow end, said elongate member having recesses at top and bottom at the wide end of said tapered end portion providing said shoulders.

8. A breakaway device as set forth in claim 7 wherein said inwardly extending means at the free end of the arms is receivable in said recesses.

9. A breakaway device as set forth in claim 8 wherein the thin flat elongate member is constituted by a tongue extending from a head, and wherein a strap is provided connected to the head, the strap having a series of holes therein for connection to a respective end of a face bow.

10. A breakaway device as set forth in claim 1 wherein the said one end of the case with the opening is the anterior end of the case.

11. A breakaway device as set forth in claim 10 comprising strap means attached to the face bow, the tension means being interposed between the strap means and the coupling member.

12. A breakaway device as set forth in claim 11 wherein the strap means has a series of holes therein for connection to a respective end of a face bow, and wherein the strap means has a plastic sleeve shrunk thereon adopted to be punctured at a hole in the strap means selected for application of the desired traction on the teeth.

13. A breakaway device comprising:

a case having anterior and posterior ends with an opening at one end thereof;

a coupling member for insertion in the case through said opening;

latch means in the case for releasably latching the coupling member inserted in the case through said opening;

said latch means comprising spring gripper means adapted resiliently to grip said coupling member and to release said coupling member for being pulled out of the case when subjected to breakaway pull exceeding a predetermined value, as determined by the spring grip of the gripper means on said member;

and means carried by the case accessible from outside the case for adjusting the grip of the spring gripper means on the coupling member to adjust the breakaway pull;

said spring gripper means comprising a spring clasp having first and second arms extending endwise in said case having free ends adjacent the said one end of the case with the opening, said arms being arranged to spring away one from the other on insertion of said coupling member between their free ends;

the arms having means extending inwardly toward one another at their free ends for releasably latching the coupling member in the case and the coupling member having shoulders facing away from said one end of the case, the arms being resiliently contractible into a contracted position wherein said inwardly extending means are latched in place with respect to the shoulders to couple the case and the coupling member together for transmission of tension as long as the tension is less than said predetermined value, the coupling member spreading the arms apart and pulling out from between the arms when a pull on the coupling members exceeds a breakaway value;

said adjusting means comprising means for adjusting the arms to vary the force required for the coupling member to spread the arms apart.

14. A breakaway device as set forth in claim 13 wherein the clasp comprises a relatively narrow strip of resilient sheet metal bent generally to V-shape, thereby having said arms diverging from an apex, and further bent to provide the said inwardly extending means at the ends of the arms, the case having a chamber therein for the clasp with the clasp being arranged in the chamber with its apex adjacent the other end of the case and with its arms extending in the case from adjacent said other end of the case to adjacent its said one end, the chamber having cam means at the top and bottom thereof engaging the top and bottom of the arms for contracting the arms on movement of the clasp relative to the case toward its said other end and allowing the arms to expand on movement of the clasp relative to the case toward its said one end, the adjusting means comprising an adjustment screw extending through said other end of the case to a connection with the apex of the clasp.

15. A breakaway device as set forth in claim 14 wherein the screw is threaded in a tapped hole in the apex of the clasp.

* * * * *